United States Patent [19]

Hsiao

[11] Patent Number: 4,556,678
[45] Date of Patent: Dec. 3, 1985

[54] SUSTAINED RELEASE PROPRANOLOL TABLET

[75] Inventor: Charles H. Hsiao, Cooper City, Fla.

[73] Assignee: Key Pharmaceuticals, Inc., Miami, Fla.

[21] Appl. No.: 391,929

[22] Filed: Jun. 24, 1982

[51] Int. Cl.⁴ ...................... A61K 31/135; A61K 9/24
[52] U.S. Cl. ........................................ 514/652; 424/19
[58] Field of Search ........................... 424/21, 330, 19; 514/652

[56] References Cited

U.S. PATENT DOCUMENTS 4,248,856 2/1981 Guley et al. ........................... 424/21

OTHER PUBLICATIONS

Chem. Abst., 94-52973e and 52962a (1981).

Primary Examiner—Stanley J. Friedman
Attorney, Agent, or Firm—Wegner & Bretschneider

[57] ABSTRACT

A method of providing a patient suffering from cardiac arrhythmia with a sustained dosage of propranolol over a prolonged period of time comprises orally administering to the patient a tablet consisting essentially of a therapeutically effective amount of propranolol to provide a sustained release thereof over a prolonged period of time which is contained in compressed granules having from about 0.1 to about 10 parts by weight hydroxypropyl methylcellulose and about one part by weight hydroxypropyl cellulose and a lubricant for the compressed granules.

2 Claims, No Drawings

SUSTAINED RELEASE PROPRANOLOL TABLET

BACKGROUND OF THE INVENTION

The present invention relates to a sustained release preparation of propranolol. Specifically, it relates to an oral dosage form which provides a release period suitable for single daily dosing while exhibiting good bioavailability.

Propranolol is a well known and widely use betaadrenergic receptor blocking agent. In the oral formulations currently in use, propranolol is almost completely absorbed from the gastrointestinal tract, but it is subject to rapid liver metabolism. Administration with food has been reported to enhance its bioavailability. The biological half-life ranges from 3 to 6 hours after oral administration.

Propranolol is effective in the treatment of hypertension, cardiac arrhythmia and angina pectoris and is indicated in the prophylaxis of common migraine headaches. It is desirable to maintain a constant plasma propranolol level to compete with available beta receptor sites thereby blocking the chronotropic and inotropic responses to catecholamines. Therapeutic doses of propranolol decreases heart rate, cardiac output and blood pressure.

SUMMARY OF THE INVENTION

A method of providing a sustained release of propranolol over a prolonged period is provided for patients suffering from hypertension, cardiac arrhythmia, and angina pectoris, and for common migrane headache prophylaxis, which comprises administering to the patient an oral sustained release dosage form. This oral sustained release dosage form is a tablet containing sufficient propranolol to provide a sustained release over a prolonged period contained in granules formed into said tablet, said tablet consisting essentially of a plurality of compressed granules consisting essentially of from about 0.1 to about 10 parts by weight hydroxypropyl methylcellulose and about one part by weight hydroxypropyl cellulose and a lubricant for said granules.

The oral sustained release dosage unit form comprises an important aspect of the present invention, permitting a sustained release of propranolol over a prolonged period of time.

DETAILED DESCRIPTION OF THE INVENTION

Included in the tablet is hydroxypropyl methylcellulose in an amount of about 20 to about 200 mg, with 50 mg being preferred. The hydroxypropyl methylcellulose has the molecular weight of about 20,000 to about 140,000, preferably about 140,000.

Also included is hydroxypropyl cellulose, present in an amount of about 20 to about 200 mg, preferably about 100 mg. The hydroxypropyl cellulose has a molecular weight in the range of from about 60,000 to about 300,000 with 60,000 being a particularly preferred embodiment.

The tablet also includes a lubricant such as magnesium stearate to aid in the tableting process. The magnesium stearate may be replaced with other suitable tablet lubricants.

The tablet to the present invention may vary widely in the amount of propranolol that is included. The therapeutic range of 40 to 480 mg per tablet is indicated to control blood pressure, angina, arrythmia and migraine, with 80 and 160 mg tablets being preferred. The oral dosage form herein described provides a release period suitable for once a day dosing.

The following non-limiting examples serve to further illustrate the invention:

EXAMPLE I

The following components are blended and granulated with an isopropyl alcohol-water (4:1) mixture:
propranolol HCl: 160 gm
hydroxypropyl methylcellulose (Methocel K4M, Dow): 50 gm (m.w. 86,000)
hydroxypropyl cellulose (Klucel LF, Hercules): 100 gm (m.w. 100,000)

The resulting granules are then dried at 50° C. and ground through a 14 mesh screen. The granulated mixture is lubricated with 3 gm (approximately 1%) magnesium stearate. The resultant granules are then compressed into capsule-shaped tablets, each weighing 313 mg.

According to U.S.P. II dissolution test methods, i.e., one hour in simulated gastric fluid followed by simulated intestinal fluid, the following data was collected:

| Time (in hours) | Percent Propranolol Released |
| --- | --- |
| 1 | 20.4 |
| 2 | 32.1 |
| 4 | 48.6 |
| 6 | 64.1 |
| 8 | 80.3 |
| 10 | 87.6 |
| 12 | 94.7 |

EXAMPLE II

To determine the effectiveness of the oral sustained release dosage form of the present invention, a 24 hour single dose study was made with a standard, commercial propranolol sustained release formulation (Inderal LA; Ayerest, marketed in Canada) which was used for comparison. Both sustained release formulations contained 160 mg propranolol. In addition, a four times daily dosage was administered with a standard non-sustained release Inderal formulation ("Reference", 40 mg Q.I.D.). The results were analyzed by plotting concentration of propranolol against time. The results of area under the concentration-time (AUC) curve are as follows:

| | AUC (mg/hr/ml) | | |
| --- | --- | --- | --- |
| Experiment | The Invention | Inderal LA | Reference |
| A | 1445 | 313 | 1041 |
| B | 1413 | 786 | 7026 |
| C | 900 | 239 | 1778 |
| D | 559 | 114 | 658 |
| Mean | 1079 | 363 | 2625 |

With respect to the comparison of the sustained release tablet of the present invention ("The Invention") versus the sustained release formulation of the prior art ("Inderal LA"), it is seen that the present invention provides a better bioavailability. The data for Experiment B, "Reference", appears skewed.

What is claimed is:

1. An oral sustained release dosage unit form tablet to provide a sustained release of propranolol over a prolonged period, said tablet consisting essentially of
   a. a therapeutically effective amount of propranolol to provide a sustained release thereof over said prolonged period contained in
   b. compressed granules consisting essentially of
      1. from about 0.1 to about 10 parts by weight hydroxypropyl methylcellulose having a molecular weight of from about 20,000 to about 140,000;
      2. about one part by weight hydroxypropyl cellulose having a molecular weight of from about 60,000 to about 300,000; and
      3. a lubricant for said granules.

2. The dosage unit form tablet of claim 1 wherein the weight ratio of hydroxypropyl cellulose to hydroxypropyl methylcellulose is about 2:1.

* * * * *